US012611099B2

(12) United States Patent
Bor et al.

(10) Patent No.: US 12,611,099 B2
(45) Date of Patent: Apr. 28, 2026

(54) PSYCHOPHYSICAL EVALUATION OF THE EFFECT OF VITREOUS FLOATERS

(71) Applicant: Alcon Inc., Fribourg (CH)

(72) Inventors: Zsolt Bor, San Clemente, CA (US); Alireza Malek Tabrizi, Fremont, CA (US)

(73) Assignee: Alcon Inc., Fribourg (CH)

( * ) Notice: Subject to any disclaimer, the term of this patent is extended or adjusted under 35 U.S.C. 154(b) by 330 days.

(21) Appl. No.: 18/351,381

(22) Filed: Jul. 12, 2023

(65) Prior Publication Data

US 2024/0016379 A1     Jan. 18, 2024

Related U.S. Application Data

(60) Provisional application No. 63/388,896, filed on Jul. 13, 2022.

(51) Int. Cl.
| | |
|---|---|
| *A61B 3/10* | (2006.01) |
| *G06T 7/00* | (2017.01) |
| *G06T 7/521* | (2017.01) |
| *G16H 30/40* | (2018.01) |

(52) U.S. Cl.
CPC .......... *A61B 3/1025* (2013.01); *G06T 7/0012* (2013.01); *G06T 7/521* (2017.01); *G16H 30/40* (2018.01); *G06T 2207/30041* (2013.01)

(58) Field of Classification Search
CPC ..... A61B 3/1025; G06T 7/521; G06T 7/0012; G06T 2207/30041; G16H 30/40
USPC ........................................................ 351/203
See application file for complete search history.

(56) References Cited

U.S. PATENT DOCUMENTS

| | | | |
|---|---|---|---|
| 3,780,979 | A | 12/1973 | De |
| 4,357,088 | A | 11/1982 | Pomerantzeff |
| 5,312,396 | A | 5/1994 | Feld |
| 5,909,270 | A | 6/1999 | Moser |
| 6,142,630 | A | 11/2000 | Koester |

(Continued)

FOREIGN PATENT DOCUMENTS

| | | |
|---|---|---|
| AU | 2018274939 B2 | 6/2020 |
| CN | 210009227 U | 2/2020 |

(Continued)

OTHER PUBLICATIONS

Adrian G.H. Podoleanu et al., Combined optical coherence tomograph and scanning laser ophthalmoscope mi nije dostupan besplatno., Electronics Letters, 34 (11), 1998.

(Continued)

*Primary Examiner* — Brandi N Thomas
*Assistant Examiner* — Boutsikaris Leonidas
(74) *Attorney, Agent, or Firm* — Patterson + Sheridan, LLP

(57)     ABSTRACT

Particular embodiments disclosed herein enable psychophysical evaluation of vitreous floaters. One or more patient stimulus images are projected onto the patient's retina, the patient images including a stationary or mobile fixation target. While the patient stimulus images are displayed, images of the patient's retina are captured, such as using an SLO, and shadow images are derived from the images. The shadow images include representations of shadows cast by floaters. Observer stimulus images are generated from the shadow images and the patient stimulus images and projected onto the retinas of an observer, such as using a virtual reality display device.

18 Claims, 10 Drawing Sheets

(56) References Cited

U.S. PATENT DOCUMENTS

| | | |
|---|---|---|
| 6,322,556 B1 | 11/2001 | Gwon |
| 6,789,900 B2 | 9/2004 | Van |
| 7,374,287 B2 | 5/2008 | Van |
| 7,510,282 B2 | 3/2009 | Ueno |
| 7,520,613 B2 | 4/2009 | Saito et al. |
| 7,703,922 B2 | 4/2010 | Van |
| 8,480,659 B2 | 7/2013 | Frey et al. |
| 8,652,602 B1 | 2/2014 | Dolla |
| 8,783,868 B2 | 7/2014 | Qiu |
| 8,876,808 B2 | 11/2014 | Feklistov et al. |
| 8,994,753 B2 | 3/2015 | Nakano |
| 9,033,500 B2 | 5/2015 | Utsunomiya |
| 9,603,519 B2 | 3/2017 | Bor et al. |
| 9,675,243 B2 | 6/2017 | Sasak et al. |
| 9,789,002 B2 | 10/2017 | Van De Velde |
| 10,130,511 B2 | 11/2018 | Dantus |
| 10,478,342 B2 | 11/2019 | Dick |
| 10,555,835 B2 | 2/2020 | Schuele et al. |
| 2007/0258094 A1 | 11/2007 | Izatt et al. |
| 2007/0291277 A1 | 12/2007 | Everett |
| 2009/0073384 A1 | 3/2009 | Warden |
| 2009/0137989 A1 | 5/2009 | Kataoka |
| 2009/0196477 A1 | 8/2009 | Cense et al. |
| 2010/0123873 A1 | 5/2010 | Raymond |
| 2010/0152847 A1 | 6/2010 | Padrick |
| 2011/0077557 A1 | 3/2011 | Wing et al. |
| 2012/0281235 A1 | 11/2012 | Murata |
| 2013/0131652 A1 | 5/2013 | Dick |
| 2013/0173029 A1 | 7/2013 | Caldeira et al. |
| 2014/0058367 A1 | 2/2014 | Dantus |
| 2014/0216468 A1 | 8/2014 | Goldshleger |
| 2014/0257257 A1 | 9/2014 | Grant et al. |
| 2014/0268036 A1 | 9/2014 | Ketterling et al. |
| 2014/0276674 A1 | 9/2014 | Lee |
| 2015/0190278 A1 | 7/2015 | Gooding |
| 2015/0342782 A1 | 12/2015 | Mordaunt |
| 2016/0058617 A1 | 3/2016 | Luttrull et al. |
| 2016/0074214 A1 | 3/2016 | Palanker et al. |
| 2016/0074221 A1 | 3/2016 | Tassignon et al. |
| 2016/0166431 A1 | 6/2016 | Vogler et al. |
| 2016/0227999 A1 | 8/2016 | An et al. |
| 2016/0235588 A1 | 8/2016 | Hart et al. |
| 2016/0256324 A1 | 9/2016 | Suzuki |
| 2016/0278629 A1 | 9/2016 | Schuele |
| 2016/0302969 A1 | 10/2016 | Yamamoto |
| 2017/0181625 A1 | 6/2017 | Kawakami et al. |
| 2017/0252213 A1 | 9/2017 | Furuuchi et al. |
| 2017/0326003 A1 | 11/2017 | Schuele et al. |
| 2018/0028354 A1 | 2/2018 | Heeren |
| 2018/0028355 A1 | 2/2018 | Raksi |
| 2018/0140257 A1 | 5/2018 | Govindjee et al. |
| 2018/0206719 A1 | 7/2018 | Adler et al. |
| 2018/0317767 A1* | 11/2018 | Ryan ..................... A61B 3/152 |
| 2018/0353064 A1 | 12/2018 | Soetikno et al. |
| 2018/0368915 A1 | 12/2018 | Xia et al. |
| 2019/0159933 A1 | 5/2019 | Romano et al. |
| 2019/0282403 A1 | 9/2019 | Barrett et al. |
| 2019/0290124 A1 | 9/2019 | Laforest et al. |
| 2019/0313903 A1* | 10/2019 | McKinnon ............ G16H 50/20 |
| 2019/0365569 A1 | 12/2019 | Skovgaard |
| 2020/0038241 A1 | 2/2020 | Wang et al. |
| 2020/0060873 A1 | 2/2020 | Heeren |
| 2020/0085292 A1 | 3/2020 | Fukuma et al. |
| 2020/0129336 A1 | 4/2020 | Schuele et al. |
| 2020/0130103 A1 | 4/2020 | Choi |
| 2020/0192080 A1 | 6/2020 | Karam |
| 2020/0196853 A1 | 6/2020 | Van Hemert et al. |
| 2020/0273218 A1 | 8/2020 | Camino et al. |
| 2020/0397289 A1 | 12/2020 | Ralston |
| 2020/0400422 A1 | 12/2020 | Ralston |
| 2021/0100450 A1 | 4/2021 | Amma |
| 2021/0186753 A1 | 6/2021 | Al-qaisi et al. |
| 2021/0275009 A1 | 9/2021 | Yates |
| 2021/0378507 A1 | 12/2021 | Wallace |
| 2021/0386586 A1 | 12/2021 | Bor |
| 2022/0012459 A1 | 1/2022 | Schwiegerling |
| 2022/0031511 A1 | 2/2022 | Charles |
| 2023/0157889 A1 | 5/2023 | Bor |
| 2024/0269001 A1* | 8/2024 | Katchinskiy ............ G06T 7/521 |

FOREIGN PATENT DOCUMENTS

| | | |
|---|---|---|
| CN | 108371542 B | 4/2020 |
| CN | 109196333 B | 12/2020 |
| CN | 111281651 B | 12/2020 |
| CN | 112862782 A | 5/2021 |
| CN | 112587302 B | 6/2021 |
| CN | 112587304 B | 6/2021 |
| DE | 19705044 A1 | 8/1998 |
| DE | 102019007147 A1 | 4/2021 |
| DE | 102019007148 A1 | 4/2021 |
| EP | 0770370 A2 | 2/1997 |
| EP | 1212022 B1 | 3/2005 |
| EP | 1563785 A1 | 8/2005 |
| EP | 1638452 B1 | 10/2006 |
| EP | 1838212 A1 | 10/2007 |
| EP | 2144552 A1 | 1/2010 |
| EP | 1928297 B1 | 11/2010 |
| EP | 2459138 A2 | 6/2012 |
| EP | 2525706 A2 | 11/2012 |
| EP | 2898820 A1 | 7/2015 |
| EP | 3061429 A1 | 8/2016 |
| EP | 2890340 B1 | 2/2017 |
| EP | 3459487 A1 | 3/2019 |
| EP | 3501463 A1 | 6/2019 |
| EP | 3636137 A1 | 4/2020 |
| EP | 3861924 A1 | 8/2021 |
| GB | 2469249 A | 10/2010 |
| JP | 5767014 B2 | 6/2015 |
| JP | 2017176558 A | 10/2017 |
| JP | 6410468 B2 | 10/2018 |
| JP | 2018196821 A | 12/2018 |
| JP | 2018196822 A | 12/2018 |
| JP | 2020022569 A | 2/2020 |
| JP | 6736304 B2 | 7/2020 |
| JP | 6839902 B2 | 2/2021 |
| RU | 2661016 C1 | 7/2018 |
| RU | 2692666 C1 | 6/2019 |
| RU | 2695629 C1 | 7/2019 |
| RU | 2710058 C2 | 12/2019 |
| RU | 2726468 C1 | 7/2020 |
| WO | 9958047 A1 | 11/1999 |
| WO | 0137769 A1 | 5/2001 |
| WO | 0195791 A1 | 12/2001 |
| WO | 2007059189 A2 | 5/2007 |
| WO | 2009033110 A2 | 3/2009 |
| WO | 2009036104 A2 | 3/2009 |
| WO | 2009039315 A2 | 3/2009 |
| WO | 2009059400 A1 | 5/2009 |
| WO | 2010117386 A1 | 10/2010 |
| WO | 2014053824 A1 | 4/2014 |
| WO | 2015131135 A1 | 9/2015 |
| WO | 2015171793 A1 | 11/2015 |
| WO | 2016033590 A1 | 3/2016 |
| WO | 2017062673 A1 | 4/2017 |
| WO | 2017196306 A1 | 11/2017 |
| WO | 2017205857 A1 | 11/2017 |
| WO | 2020074532 A1 | 4/2020 |
| WO | 2020180729 A1 | 9/2020 |
| WO | 2020215359 A1 | 10/2020 |
| WO | 2020216763 A1 | 10/2020 |
| WO | 2020257711 A1 | 12/2020 |
| WO | 2021023799 A1 | 2/2021 |
| WO | 2021049243 A1 | 3/2021 |
| WO | 2021066047 A1 | 4/2021 |
| WO | 2021092211 A1 | 5/2021 |
| WO | 2021183637 A1 | 9/2021 |
| WO | 2022149028 A1 | 7/2022 |
| WO | 2023089416 A1 | 5/2023 |

(56)                    References Cited

FOREIGN PATENT DOCUMENTS

WO          2023089459 A1      5/2023
WO          2023097391 A1      6/2023

OTHER PUBLICATIONS

Chi-Hung Lee, et al., Imaging vitreous floaters and cataracts with optical simulations, Optik, 194, 1-9, 2019.
Christy K. Sheehy et al., High-speed, image-based eye tracking with a scanning laser ophthalmoscope, Biomedical Optics Express, vol. 3, No. 10, 2012.
D. H. Kelly, "Retinal Inhomogeneity. II. Spatial Summation," J. Opt. Soc. Am., pp. 114-119, vol. 1, No. 1 (Jan. 1984).
D. H. Kelly, "Retinal Inhomogeneity. III. Circular-Retina Theory," D.H. Kelly, J. Opt. Soc. Am., pp. 810-819, vol. 2, No. 6 (Jun. 1985).
D.H. Kelly, "Visual Processing of Moving Stimuli," J. Opt. Soc. Am., pp. 216-225, vol. 2, No. 2 (Feb. 1985).
D.H. Kelly,, "Motion and Vision. II. Stabilized Spatio-Temporal Threshold Surface," J. Opt. Soc. Am., pp. 1340-1349, vol. 69, No. 10 (Oct. 1979).
D.H.Kelly, "Retinal Inhomogeneity. I. Spatiotemporal Contrast Sensitivity," J. Opt. Sec. Am., pp. 107-113, vol. 1, No. 1 (Jan. 1984).
Mojana F. et al.. Observations by spectral-domain optical coherence tomography combined with simultaneous scanning laser ophthalmoscopy: imaging of the vitreous, American Journal of Ophthalmol. Apr. 2010;149(4):641-650.
Nidek, Scanning Laser Ophthalmoscope Mirante SLO/OCT Mirante SLO, https://www.nidek-intl.com/product/ophthaloptom/diagnostic/dia_retina/mirante.htm.
Peter G. J. Barten, "Contrast Sensitivity of the Human Eye and its Effects on Image Quality," Chapter 3, pp. 27-40, Model for the spatial contrast sensitivity of the eye, (1999).
Pointer, J. S., & Hess, R. F. "The contrast sensitivity gradient across the human visual field: With emphasis on the low spatial frequency range,", R. F. Vision Research, 29(9), 1133-1151 (1989).
Sebag J et al., Vitreous and Vitreoretinal Interface, Ch. 21, 2015.
Sebag J., Vitreous and Vision Degrading Myodesopsia. Progress in Retinal and Eye Research Nov. 2020;79.
T Ivanova et al, Vitrectomy for primary symptomatic vitreous opacities: an evidence-based review, Eye (Lond) May 2016;30(5):645-55.
Teri T Kleinberg et al., Vitreous substitutes: a comprehensive review, Survey of Ophthalmology, 56 (4), 2011.
Blake F. Webb, et al.; "Prevalence of vitreous floaters in a community sample of smartphone users"; International Journal of Ophthalmology; Jun. 18, 2013; pp. 402-405; 6(3); PMC/ US National Library of Medicine National Institutes of Health.
Chirag P. Shah, et al., YAG Laser Vitreolysis vs Sham YAG Vitreolysis for Symptomatic Vitreous Floaters A Randomized Clinical Trial, JAMA Ophthalmology, Sep. 2017, 918-923, 135-9.
Damodaran et al., "Digital micromirror device based ophthalmoscope with concentric circle scanning", vol. 8, No. 5, pp. 2766-2780, 2017, Biomedical Optics Express.
ELLEX Website, Treatment Guidelines—Laser Floater Removal; 2016, Ellex Medical Pty Ltd. E&OE. VB0002E, downloaded Apr. 20, 2017.
Felix Sauvage et al: "Photoablation of Human Vitreous Opacitiesby Light—Induced Vapor Nanobubbles", ACS Nano, vol. 13, No. 7, Jul. 9, 2019, pp. 8401-8416.
Fischer et al., "Scanning Laser Ophthalmoscopy (SLO)", In: Bille JF, editor. High Resolution Imaging in Microscopy and Ophthalmology: New Frontiers in Biomedical Optics [Internet], accessed on Jan. 30, 2023 from https://www.ncbi.nlm.nih.gov/books/NBK554043, Aug. 14, 2019, Springer.
Ginner et al., "Wide-Field OCT Angiography at 400 KHz Utilizing Spectral Splitting", Photonics, vol. 1, No. 4, pp. 369-379, Oct. 23, 2014.
Heidelberg Engineering GMBH, "Spectralis. Hardware Operating Instructions," Version 001, Aug. 2007.

Heidelberg Engineering, "Spectralis. Multimodal Imaging Platform Optimized for the Posterior Segment", accessed on Jan. 30, 2023 from https://business-lounge.heidelbergengineering.com/US/en/products/spectralis/spectralis/.
Hofer et al., "Dispersion encoded full range frequency domain optical coherence tomography", vol. 17, No. 1, pp. 7-24, Jan. 5, 2009, Optics Express, US.
Hofer et al., "Fast dispersion encoded full range optical coherence tomography for retinal imaging at 800 nm and 1060 nm", vol. 18, No. 5, pp. 4898-4919, Mar. 1, 2010, Optics Express.
Kim Jihwan et al. "Nonmechanical Laser Beam Steering Based on Polymer Polarization Gratings: Design Optimization and Demonstration", Journal of Lightwave Technology, vol. 33, No. 10, pp. 2068-2077, May 15, 2015.
Leitgeb et al., "Complex ambiguity-free Fourier domain optical coherence tomography through transverse scanning", vol. 32, pp. 3453-3455, 2007, Optics Letters.
Li et al., "DMD-based three-dimensional chromatic confocal microscopy", vol. 59, No. 14, pp. 4349-4356, 2020, Applied Optics.
Martial et al., "Programmable Illumination and High-Speed, Multi-Wavelength, Confocal Microscopy Using a Digital Micromirror", vol. 7, No. 8, e43942, Aug. 2012, PLOS ONE.
Michael J. Escuti, et al., "Geometric-Phase Holograms", Optics & Photonics News, pp. 22-29, Feb. 2016.
Milston Rebecca et al: "Vitreous floaters: Etiology, diagnostics, and management", Survey of Ophthalmology, vol. 61, No. 2, Mar. 1, 2016, pp. 211-227.
Nicusor Iftimia et al: "Hybrid retinal imaginer using line-scanning laser ophthalmoscopy and spectral domain optical coherence tomography", Optics Express, vol. 14, No. 26, Dec. 22, 2006.
Reece Bergstrom, et al., Vitreous Floaters, National Center for Biotechnology Information, May 21, 2020, 4 pages, Bookshelf ID NBK470420, StatPearls Publishing LLC, online.
Reznicek Lukas et al., "Wide-Field Megahertz OCT Imaging of Patients with Diabetic Retinopathy", Journal of Diabetes Research, 2015, 5 pages.
Ruggeri et al., "Imaging and full-length biometry of the eye during accommodation using spectral domain OCT with an optical switch", vol. 3, No. 7, pp. 1506-1520, Jul. 1, 2012, Biomedical Optics Express.
Sarunic et al., "Instantaneous complex conjugate resolved spectral domain and swept-source OCT using 3x3 fiber couplers", vol. 13, No. 3, pp. 957-967, Feb. 2005, Optics Express.
Shields et al., "Wide-angle Imaging of the Ocular Fundus", Review of the Ophthalmology, Feb. 15, 2003.
Singh, "Lasers Take Aim At Floaters", Ophthalmology Management, vol. 23, pp. 38, 40-42, 59, Jul. 1, 2019.
Singh, "Modern vitreolysis—YAG laser treatment now a real solution for the treatment of symptomatic floaters", Survey of Ophthalmology, vol. 65, No. 5, pp. 581-591, Mar. 3, 2020.
SunLED, NanoPoint-0201 Series LEDs, published Feb. 15, 2016, www.SunLEDusa.com.
Volk Optical, "Volk Idrees Mid-Vitreous Lens", accessed on Dec. 20, 2020 from https://www.volk.com/...s?pr_prod_strat=collection_fallback&pr_rec_pid=4513049018402pr_ref_pid=4513048952866&pr_seq=uniform, Dec. 20, 2020.
Volk Optical, "Volk Singh Mid-Vitreous Lens", accessed on Dec. 20, 2020 from https://www.volk.com/products/singh-mid-vitreous-vitreous-slit-lamp-lens?_ pos=3&amp;amp;_sid=b50c0674f&amp;amp;_ss=r, Dec. 20, 2020.
Wang et al., "In vivo full range complex Fourier domain optical coherence tomography", vol. 90, 054103, Jan. 30, 2007, Applied Physics Letters.
Wikipedia Encyclopedia, Floater, Wikipedia Encyclopedia, Mar. 29, 2021, online: https://en.wikipedia.org/wiki/rloater?wprov=sfti 1.
Wojtkowski et al., "Full range complex spectral optical coherence tomography technique in eye imaging", vol. 27, No. 16, pp. 1415-1417, 2002, Optics Letters.
Yasuno et al., "Simultaneous B-M-mode scanning method for real-time full-range Fourier domain optical coherence tomography", vol. 45, No. 8, pp. 1861-1865, 2006, Applied Optics.

(56) References Cited

OTHER PUBLICATIONS

Zhang et al., Removal of a mirror image and enhancement of the signal-to-noise ratio in Fourier-domain optical coherence tomography using an electro-optic phase modulator, vol. 30, No. 2, Jan. 15, 2005, Optics Letters.

Zhang Yunbo et al: "Parallel large-range scanning confocal microscope based on a digital micromirror device", Optik vol. 124, No. 13 (2013), Aug. 4, 2012, pp. 1585-1588.

Zhou et al., "Dual channel dual focus optical coherence tomography for imaging accommodation of the eye", vol. 17, No. 11, pp. 8947-8955, May 25, 2009, Optics Express.

* cited by examiner

200

206

204

Stationary Fixation Target 602

Bright Homogeneous Background 604

Grid to Help Identify Visual Directions 606

600

PSYCHOPHYSICAL EVALUATION OF THE EFFECT OF VITREOUS FLOATERS

CROSS-REFERENCE TO RELATED APPLICATIONS

This application claims benefit of and priority to U.S. Provisional Patent Application No. 63/388,896, filed Jul. 13, 2022, the entire contents of which are incorporated by reference herein in its entirety.

BACKGROUND

Light received by the human eye, passes through the transparent cornea covering the iris and pupil of the eye. The light is transmitted through the pupil and is focused by a crystalline lens positioned behind the pupil in a structure called the capsular bag. The light is focused by the lens onto the retina, which includes rods and cones capable of generating nerve impulses in response to the light. The space between the lens and the retina is occupied by a clear gel known as the vitreous.

Through various causes, floaters may be present in the vitreous. A floater is typically formed of a clump of cells or other tissue and is more opaque than the surrounding vitreous. Floaters cast shadows onto the retina that cause visual disturbance for a patient, which can be quite severe in some patients.

It would be an advancement in the art to facilitate the treatment of floaters.

BRIEF SUMMARY

The present disclosure relates generally to a system for performing psychophysical evaluation of vitreous floaters.

Particular embodiments disclosed herein provide a method and corresponding apparatus, the method including receiving, by a computing device, one or more images of at least one of a patient's eyes. The computing device identifies one or more shaded regions in the one or more images to obtain one or more shadow images. The computing device outputs, to a display device, one or more observer stimulus images derived from the one or more shadow images to a display device.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1:
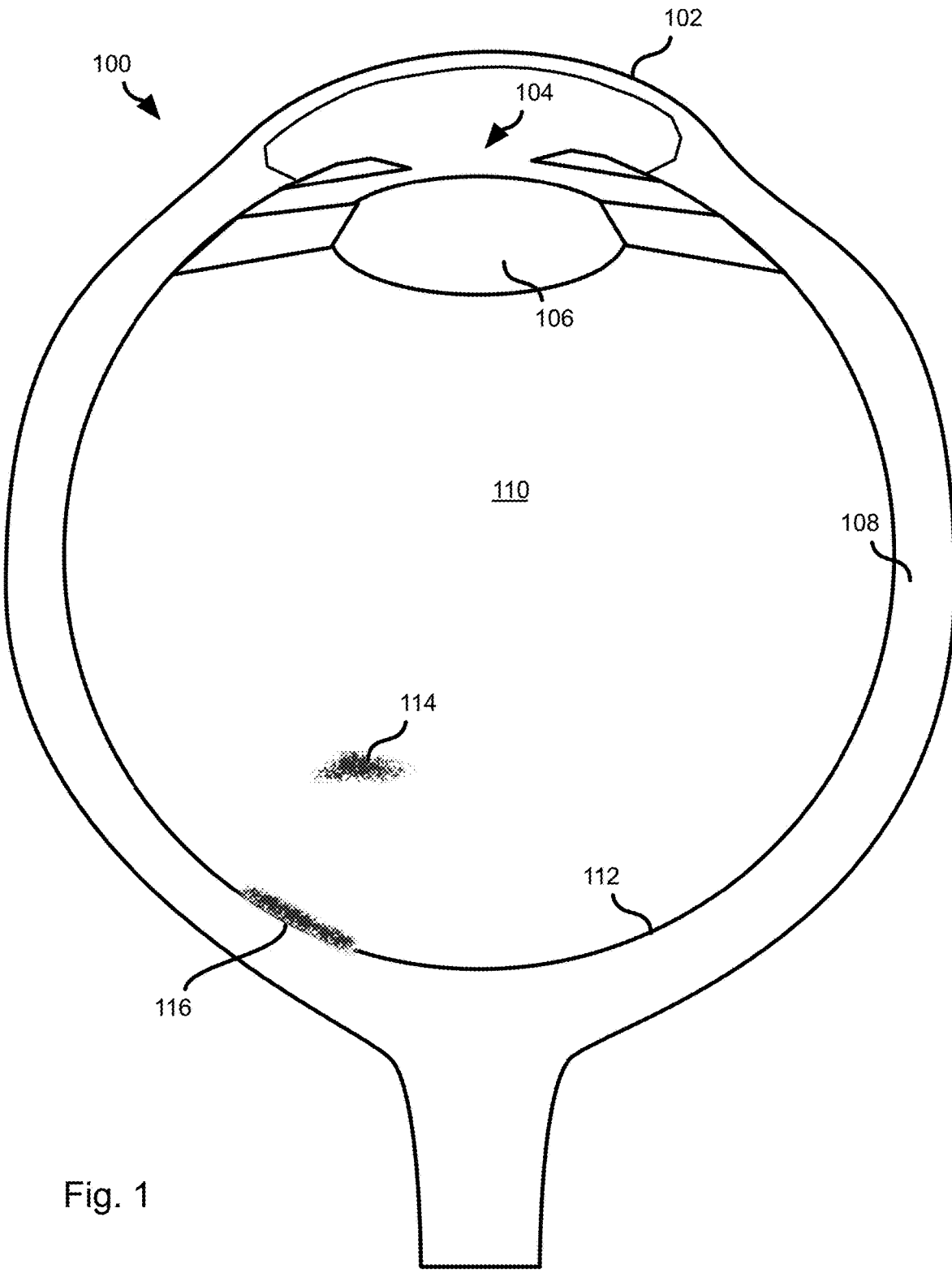
FIG. 1 is a schematic cross-sectional representation of an eye having a floater.

Referring to FIG. 1, a human eye 100 includes the cornea 102, which is a sphere-like transparent layer through which light enters the eye 100. The light then passes through the anterior chamber 138, pupil 104, and lens 106 of the eye 100, respectively. The remaining volume of the globe 108 of the eye 100, known as the posterior or vitreous chamber 140, is occupied by a clear gel known as the vitreous 110. The light is focused by the cornea 102 and lens 106 onto the retina 112 at the back of the eye 100 through the vitreous 110.

Vitreous floaters 114 are clumps of cells, collagen fibers, or other contaminants within the vitreous 110. When present, a vitreous floater 114 will cast a shadow 116 onto the retina 112. The shadow 116 may occupy an angular extent of the field of vision of the eye 100. When sufficiently large, opaque, and/or numerous, floaters 114 can significantly disturb the patient's vision.

Figure 2A:
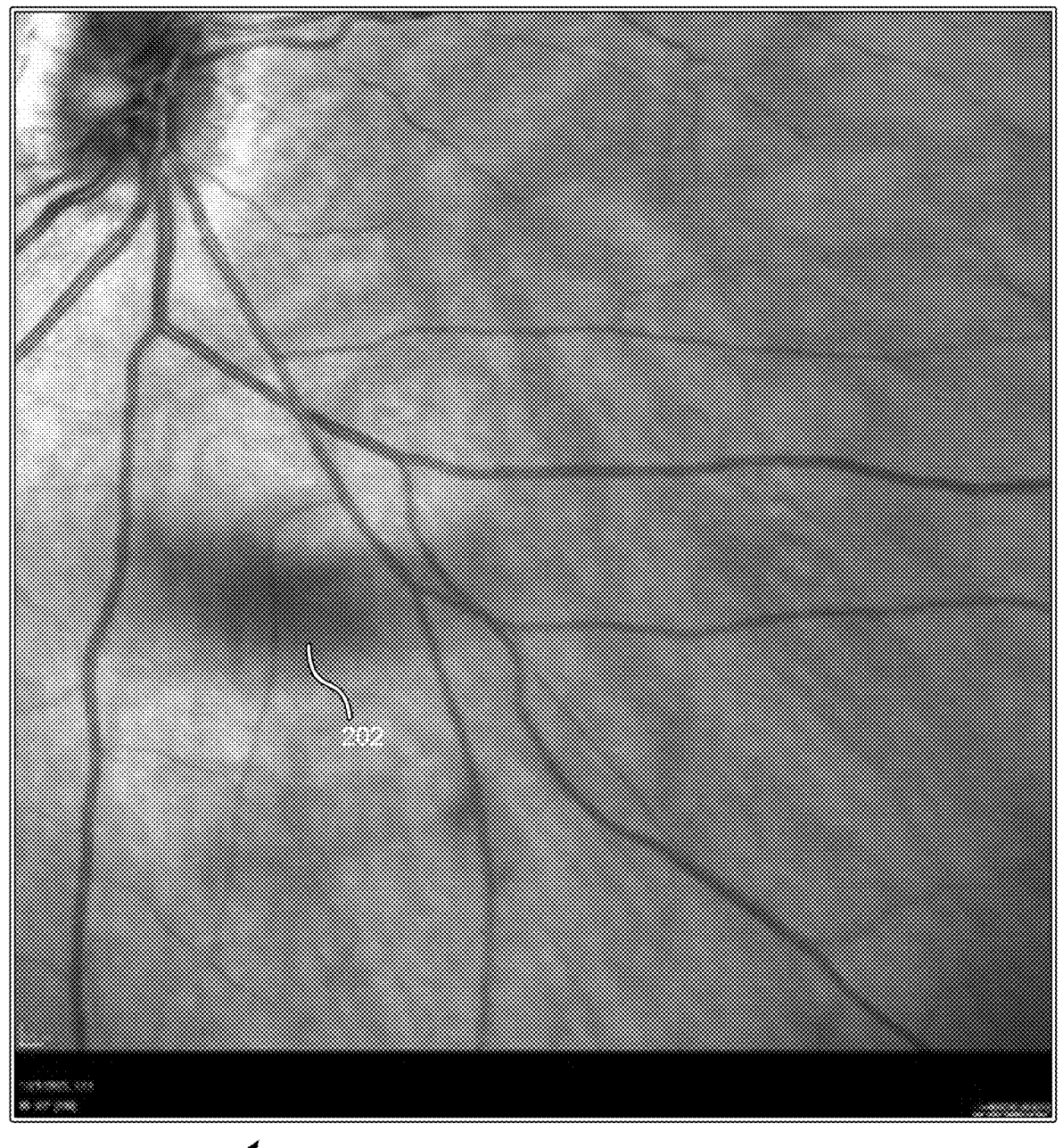
FIG. 2A is an image of a retina having shadows caused by vitreous floaters.

Referring to FIG. 2A, an image 200 of the retina 112 may be obtained, such as using a scanning laser ophthalmoscope (SLO), a fundus camera, optical coherence tomography (OCT) device, or other imaging modality. A portion of the light transmitted onto the retina 112 to capture the image 200 will be scattered by any floaters 114 disposed in the vitreous 110 resulting in a one or more shadows 202 being present in the image 200.

The one or more shadows 202 may be identified as having contrasting pixel intensity relative to the area surrounding the shadows 202. Floaters 114 tend to be motile such that one or more shadows 202 may be identified in the image 200 as having a different intensity relative to the intensity of the shadows 202 in a prior or following image in a series of video images including the image 200. For example, each image in the series of images may be registered with respect to reference features of the retina, such as a pattern of vasculature (e.g., veins) of the retina, in order to compensate for eye movement. In such an example, changes from one registered image to another may therefore correspond to changes in shadows 116 of floaters 114. The one or more shadows 202 may be identified using any approach for detecting moving objects relative to a stationary background with compensation for eye movement being performed in the same manner that such approaches use to compensate for camera movement. Still or video images 200 may also be analyzed using a machine learning model trained to identify the one or more shadows 202 corresponding to floaters 114.

Figure 2B:
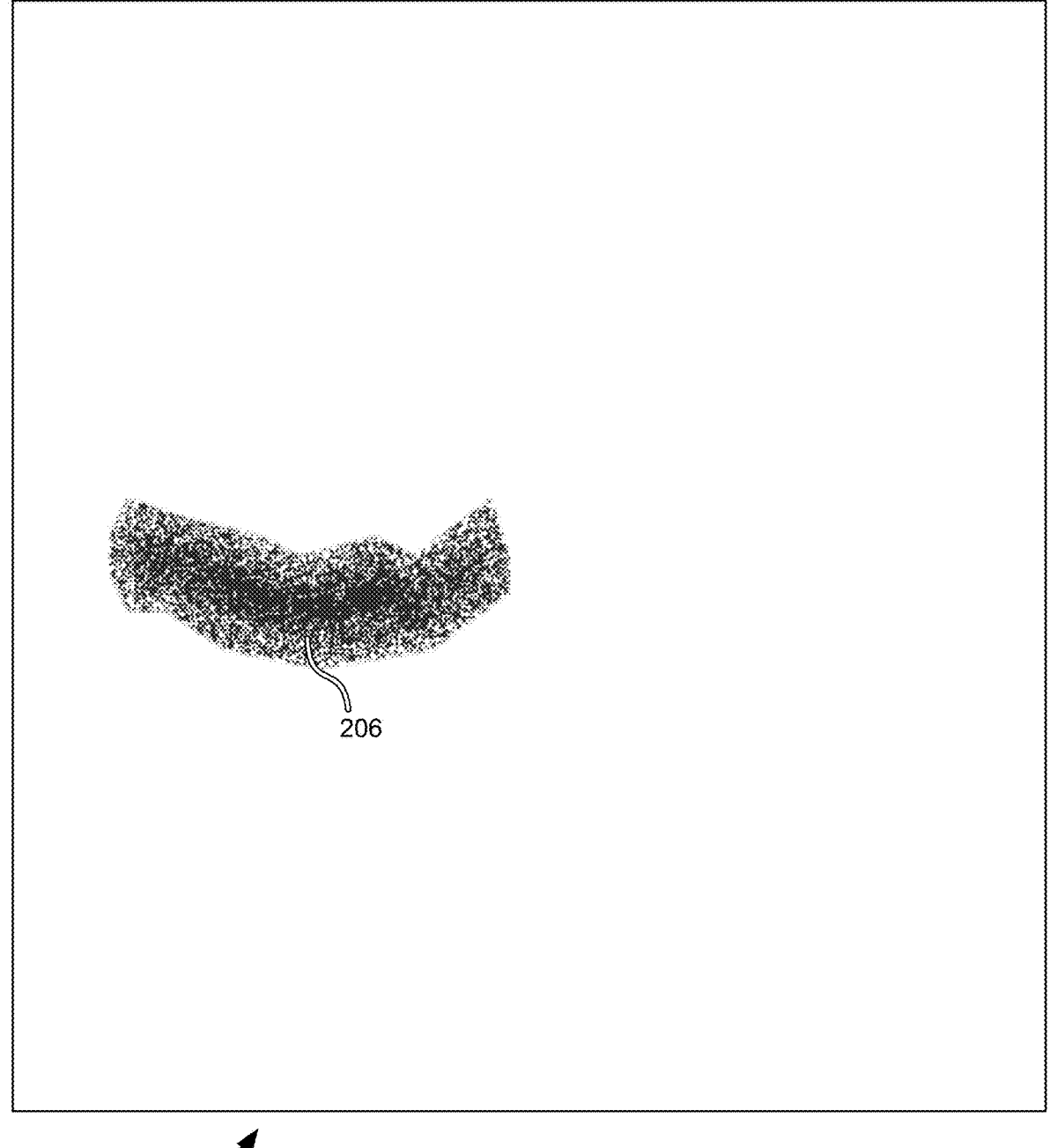
FIG. 2B is an image of a shadow from a vitreous floater extracted from the image of the retina, in accordance with certain embodiments.

Referring now to FIG. 2B, a shadow image 204 may be generated that includes only one or more shadows 206 extracted from the image 200 and corresponding to the one or more shadows 202 present in the image 200. The shadow image 204 may be an image in which all pixels are white, transparent, or some other reference color except for those pixels representing the one or more shadows 202. The pixels of the one or more shadows 206 may have an intensity indicating an estimated degree of light blockage at a corresponding point in the shadow image 204. For example, where all the pixels of the shadow image 204 are white other than the pixels of the one or more shadows 206, the difference between the intensity of the white pixels and a given pixel of the one or more shadows 206 indicates the darkness of the shadow(s) 202 represented by the given pixel of the one or more shadows 206.

Figure 3:
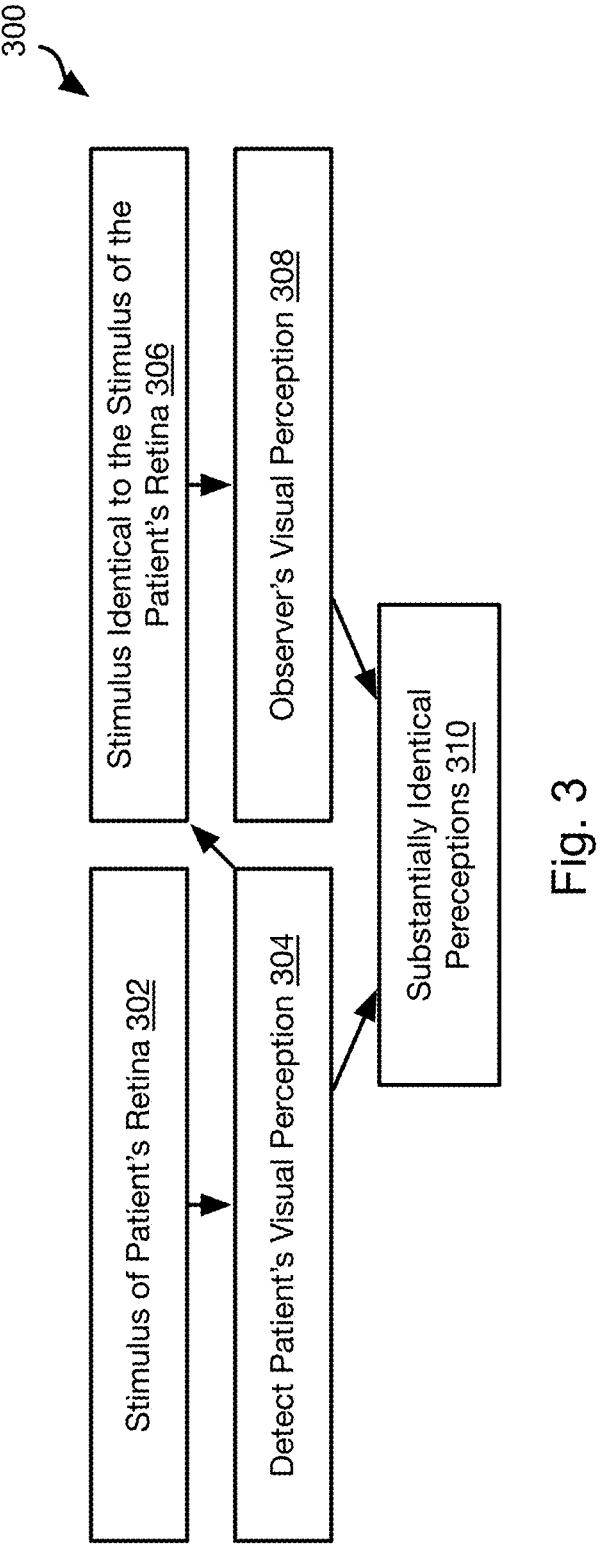
FIG. 3 is a process flow diagram of a method for performing psychophysical evaluation of vitreous floaters, in accordance with certain embodiments.

FIG. 3 illustrates a method 300 for performing psychophysical evaluation of vitreous floaters. As used herein, "psychophysical evaluation" refers to a process that enables an observer, such as a trained medical professional, to accurately perceive the shadows 116 cast by floaters 114 onto the retina 112 of a patient in order to determine the effect of the floaters 114 on the visual acuity of the patient.

In the method 300, a patient's retina 112 is first stimulated at step 302 and the patient's visual perception of the stimulus is detected at step 304. At step 306, the observer receives a stimulus that is substantially identical to the stimulus of the patient's retina 112, which is a combination of the stimulus input to the patient's eye and the perception of the patient's stimulus detected at step 304. At step 308, the observer visually perceives 308 the observer's stimulus from step 306 in order to achieve substantially identical perceptions between the patient and the observer at step 310.

Figure 4:
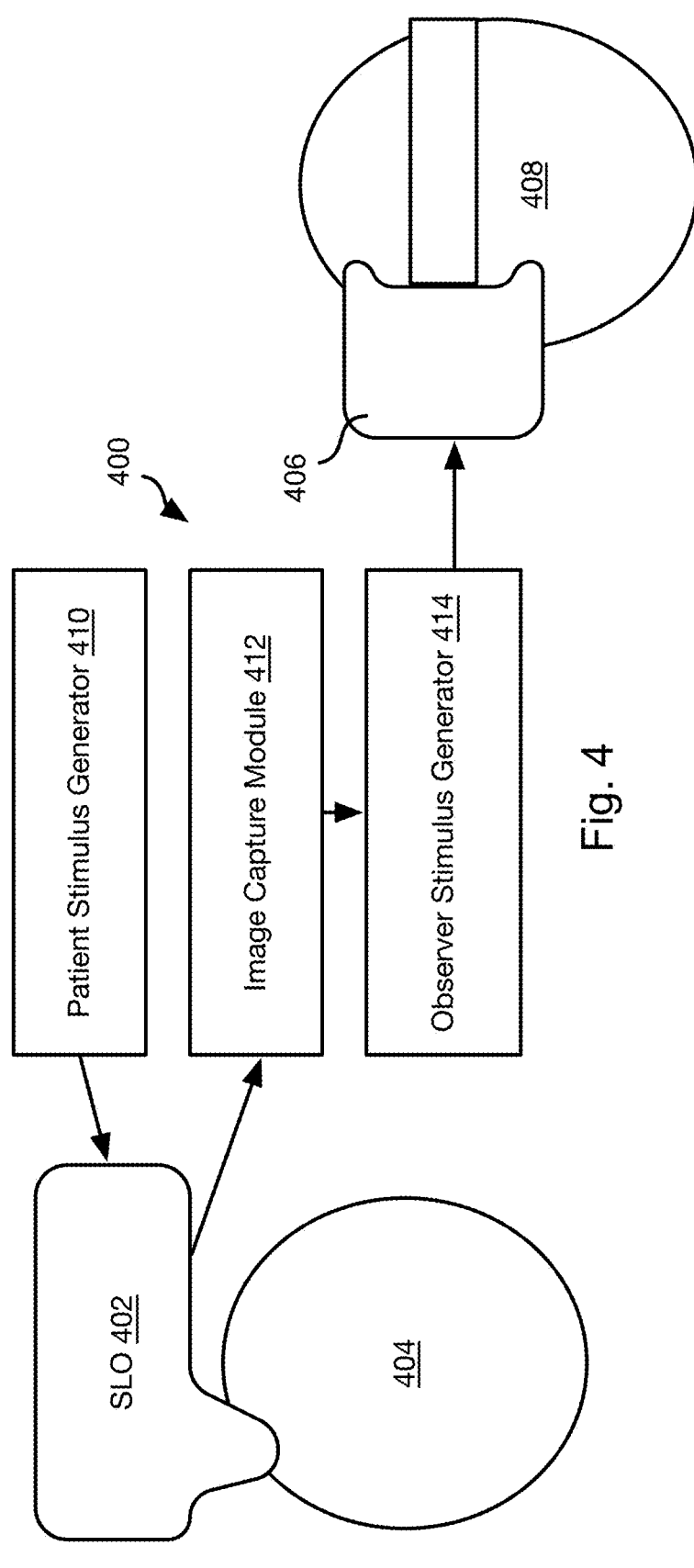
FIG. 4 is a schematic block diagram of components for performing psychophysical evaluation of vitreous floaters, in accordance with certain embodiments.

FIG. 4 illustrates a system 400 for performing psychophysical evaluation of vitreous floaters. The system 400 may include a scanning laser ophthalmoscope (SLO) 402 for both stimulating and observing the retinas 112 of the patient 404. The system 400 likewise includes a display device 406 for projecting the observer's stimulus onto the retinas of the observer 408. For example, the display device 406 may be a virtual reality (VR) display enabling projection of an image of the patient's right retina onto the observer's right retina using a right side of the VR display and projection of an image of the patient's left retina onto the observer's left retina using a left side of the VR display.

The system 400 includes a patient stimulus generator 410, an image capture module 412, and observer stimulus generator 414 that may each be implemented in a separate computing device (e.g., a computing device 900 described below with respect to FIG. 9) or using computing capabilities integral to one or both of the SLO 402 and the display device 406.

The patient stimulus generator 410 generates a patient stimulus image to be projected onto the patient's retinas 112. The patient stimulus image may have a known brightness and includes a fixation target. In some embodiments, the patient stimulus generator 410 may generate a series of images with the fixation target at a different location in each image of the series of images, thereby providing a mobile fixation target. The one or more patient stimulus images may comprise a shape (e.g., square, rectangle, or circle) of uniform color and brightness, or may be a more detailed image, e.g., an image of an indoor or outdoor setting, an image including text, or other type of image. The patient stimulus generator 410 may use existing capabilities of the SLO 402 to display the one or more stimulus images or may use one or more separate projecting devices to project the one or more patient stimulus images onto the retinas 112 of the patient.

The image capture module 412 captures images of the patient's retinas 112 during stimulation with the one or more patient stimulus images projected by the patient stimulus generator 410. The image capture module 412 may receive the images from the SLO 402, which may generate the images by scanning the retinas 112 of the patient using an infrared laser. The image capture module 412 may further isolate shadows 202 from one or more images 200 received from the SLO 402 to obtain one or more shadow images 204 as described above.

The observer stimulus generator 414 generates one or more observer stimulus images from the one or more shadow image 204. The observer stimulus generator 414 may adjust some or all of the size, brightness, contrast, or other properties of the one or shadow images 204 to obtain the one or more observer stimulus images. The adjustments performed by the observer stimulus generator 414 may be predefined adjustments based on the properties of the display device 406 in order to more closely approximate the viewing experience of the patient 404. For example, the size, brightness, contrast, or other properties may be adjusted to be within at least five percent of these properties as perceived by the patient.

The observer stimulus images may then be displayed on the display device 406 to the observer 408. Where multiple patient stimulus images were captured, the observer stimulus images may be displayed at the same frame rate at which the patient stimulus images were captured. The display of the one or more observer stimulus images may be performed substantially simultaneously with capture of the images 200, i.e., subject to delays for processing and data transmission. Alternatively, the one or more observer stimulus images or any of the images used to obtain the one or more observer stimulus images may be stored for later display or processing and display.

Figure 5:
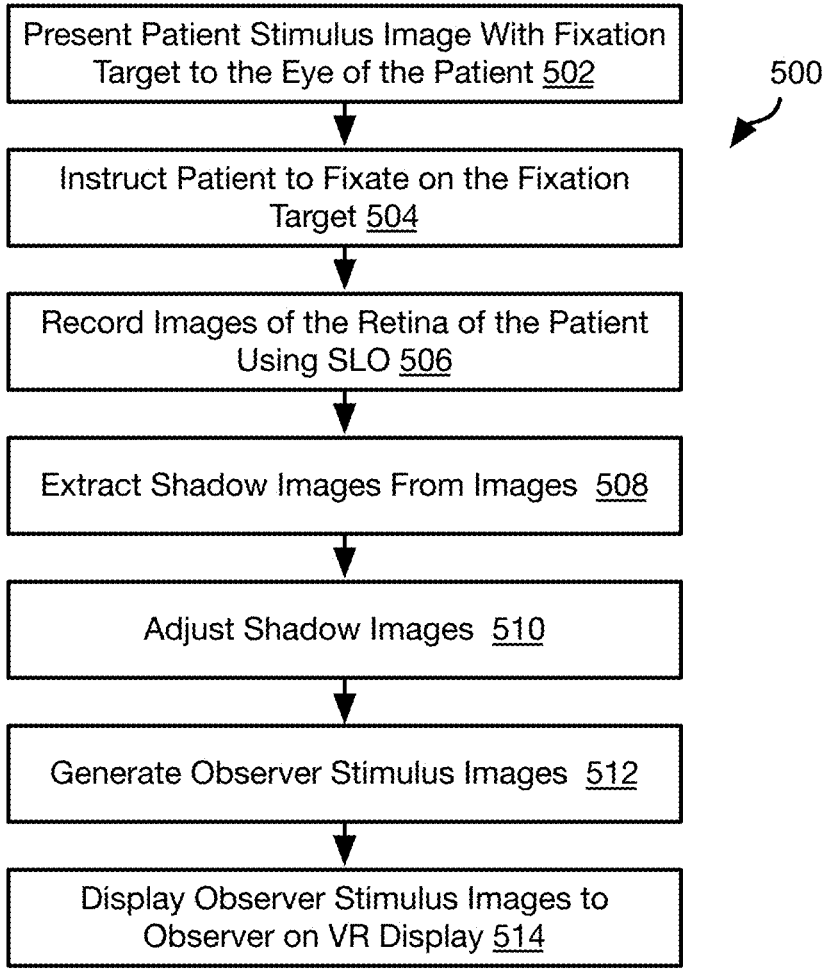
FIG. 5 is a process flow diagram of a method for performing psychophysical evaluation of vitreous floaters using a virtual reality display, in accordance with certain embodiments.

FIG. 5 illustrates a method 500 for performing psychophysical evaluation of vitreous floaters. The method 500 may be performed by a computing device 900 in cooperation with the SLO 402 and display device 406 shown in FIG. 4. The method 500 includes presenting, at step 502, one or more patient stimulus images to the retinas 112 of a patient. The patient is instructed, at step 504, to fixate on a fixation target in the one or more patient stimulus images. While presenting the one or more patient stimulus images, the method 500 includes recording, at step 506, one or more images 200 of the patient's retina using the SLO 402. For example, for each patient stimulus image, an image 200 may be captured using the SLO 402 of each retina 112 while the each patient stimulus image is being projected onto the retinas 112 of the patient.

The method 500 includes extracting, at step 508, one or more shadow images, e.g., images 204, from the one or more images 200 received from the SLO 402. The method 500 may further include adjusting, at step 510, the one or more shadow images to obtain one or more adjusted images. The one or more adjusted images may then be used to generate, at step 512, observer stimulus images.

Adjusting the one or more shadow images may include adjusting the brightness, contrast, size, or other property of the one or more shadow images such that, when displayed on the display device 406, the one or more adjusted images will closely approximate to the observer the visual perception of the patient. Generating the observer stimulus images may include combining each adjusted image with the corresponding patient stimulus image, which may also be adjusted in terms of brightness, contrast, size, or other property in order to ensure similar perception when displayed on the display device 406. In some implementations, the one or more shadow images will capture only the shadows 202 such that the one or more patient stimulus image, or an adjusted version thereof, will be combined with the one or more adjusted images in order to replicate the patient's perception of the one or more patient stimulus images. The patient stimulus image corresponding to an adjusted image may be the patient stimulus image that was displayed when capturing the image 200 that was adjusted to obtain the adjusted image.

The method 500 may then include displaying, at step 514, the one or more observer stimulus images on the display device 406. Where the one or more observer stimulus images include a plurality of observer stimulus images, the observer stimulus images may be displayed at a same frame rate at which the patient stimulus images were displayed to the patient, or at a different frame rate.

Figure 6:
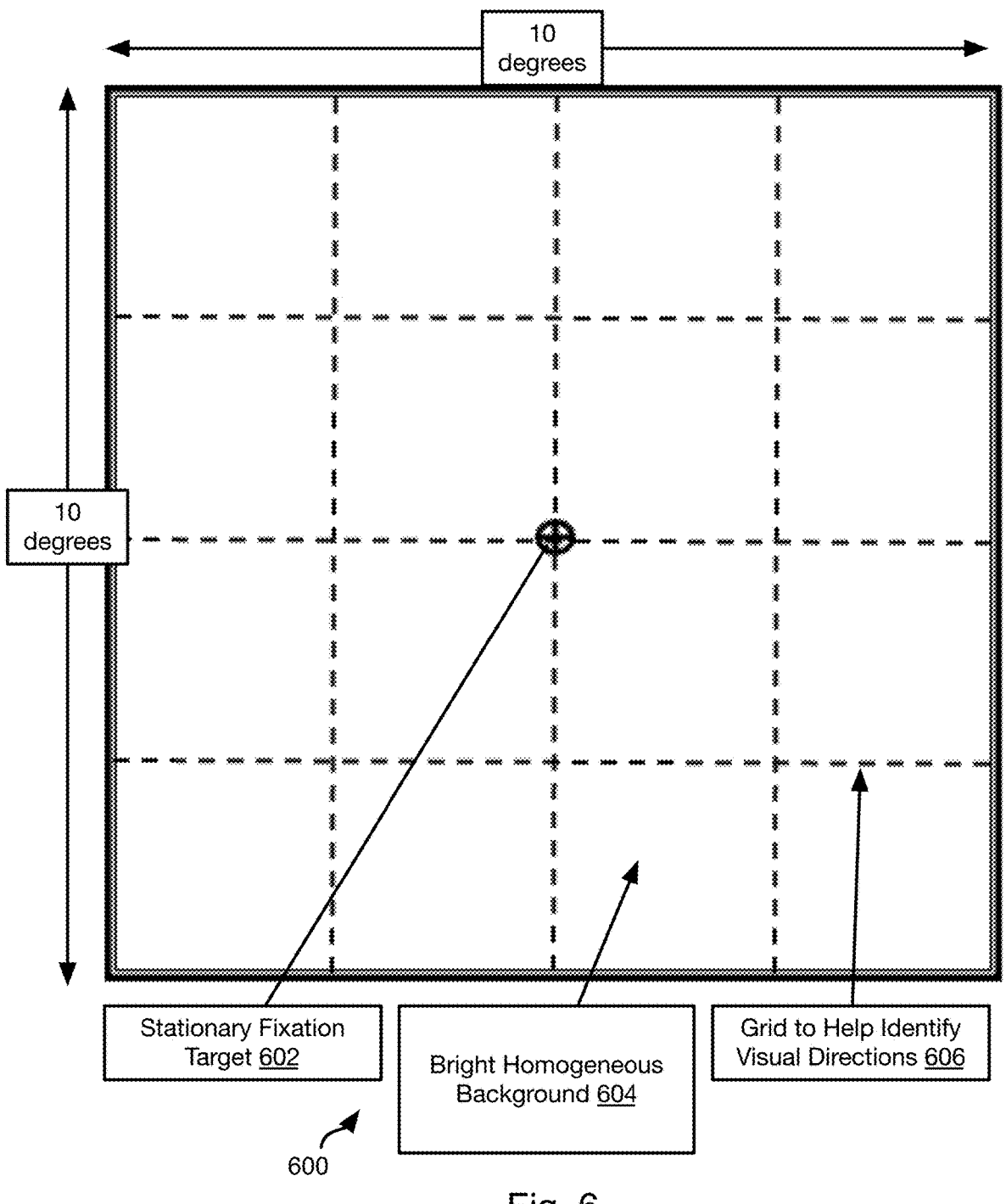
FIG. 6 is an example stimulus image, in accordance with certain embodiments.
Figure 7:
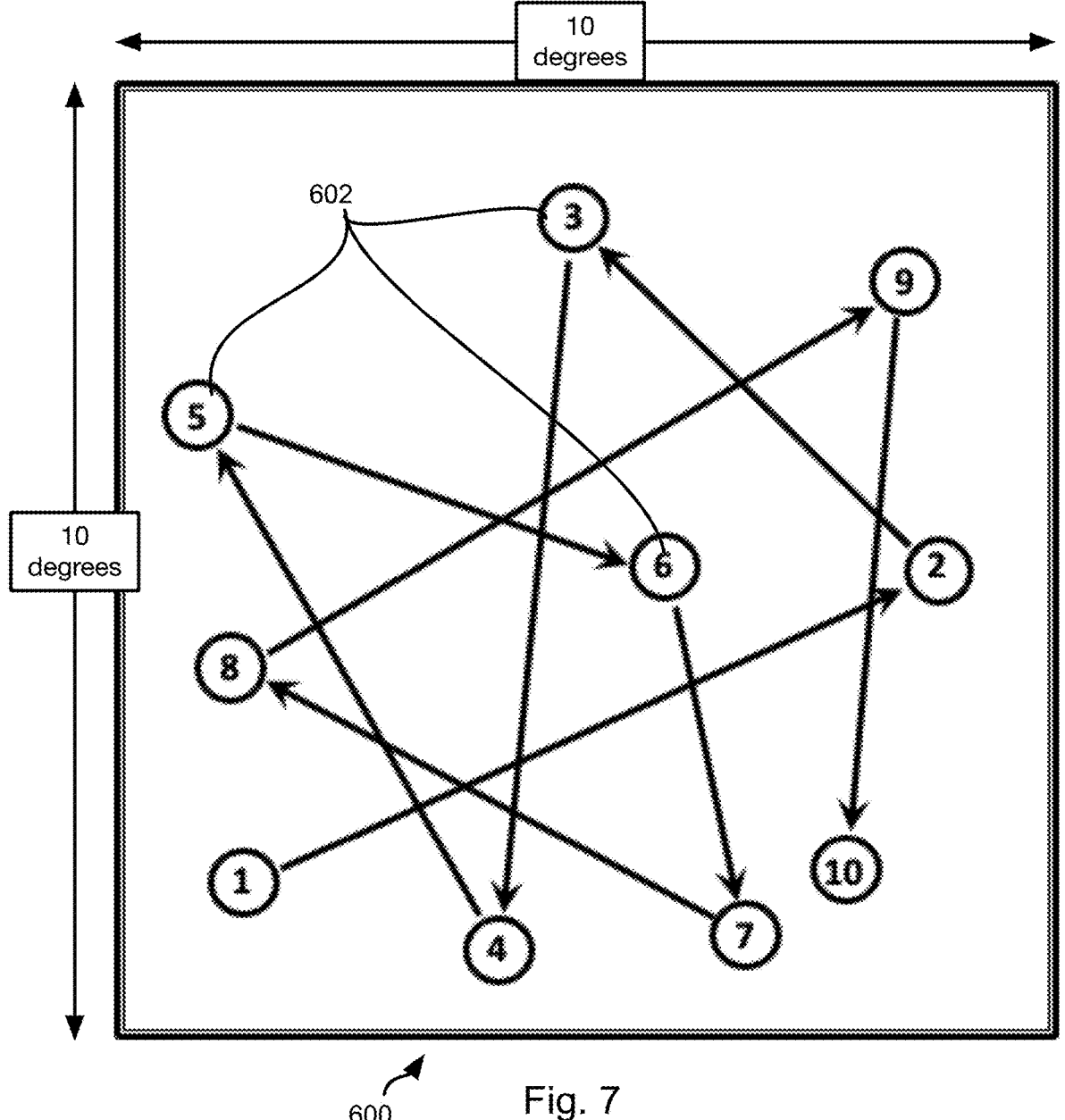
FIG. 7 is an example stimulus image with random fixation point movement, in accordance with certain embodiments.
Figure 8:
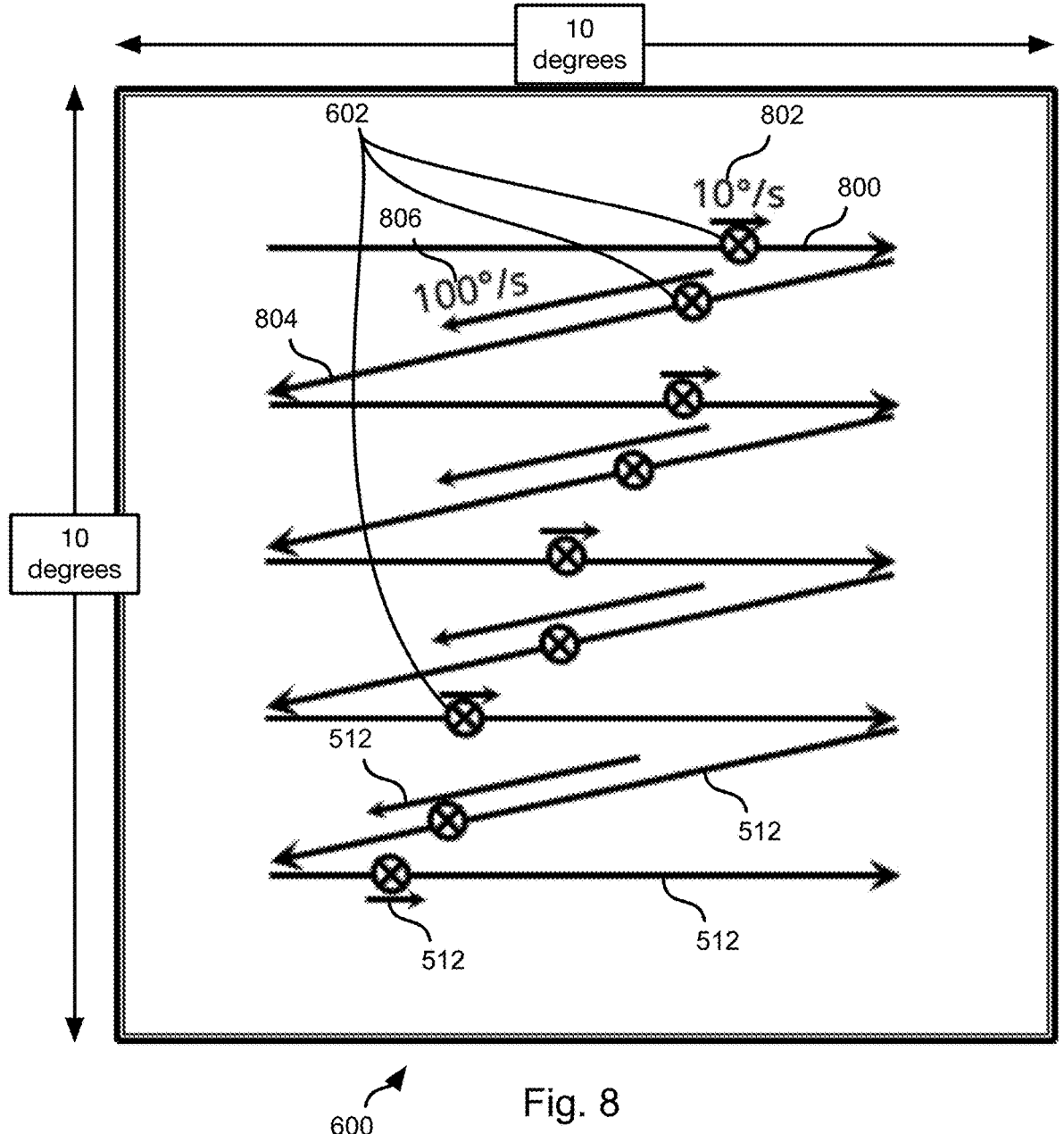
FIG. 8 is an example stimulus image with fixation point movement simulating eye movement while reading, in accordance with certain embodiments.

FIGS. 6, 7, and 8 illustrate example patient stimulus images. The corresponding observer stimulus images may have the same features with shadow images superimposed thereon, as described above.

FIG. 6 illustrates a first example patient stimulus image 600. In some implementations, the patient stimulus image 600 has a width and a height occupying between 6 and 14 degrees, between 8 and 12 degrees, or 10 degrees of a field of view of the patient. The patient stimulus image 600 includes a stationary fixation target 602, which may be in the form of crosshairs or other image visible to the patient. The patient stimulus image 600 may include a bright homogenous background 604 occupying the majority, such as at least 90 percent, or at least 95 percent, of the patient stimulus image 600. The homogeneous background may have a luminance upon display to the patient sufficient to create perceptible shadows 116 if floaters 114 are present. However, the luminance is preferably not so great that the shadows 116 are washed out and imperceptible. Likewise, the luminance is preferably not so great as to cause patient discomfort or retinal damage. For example, the luminance may be between about 250 and about 350 cd/m² (candela per square meter), such as about 300 cd/m².

A grid 606 may be included in the patient stimulus image 600 in order to facilitate determining a direction and degree of movement of shadows in the one or more observer stimulus images. For example, the grid 606 may divide each dimension (vertical and horizontal) of the patient stimulus image 600 into between three and ten segments, such as the illustrated three lines in each dimension dividing the patient stimulus image 600 into four segments for each dimension.

Referring to FIG. 7, in some implementations, a series of patient stimulus images 600 are presented at a predefined frame rate. The fixation target 602 may be in a plurality of different positions in the series of patient stimulus images 600. For example, the illustrated numerals 1 to indicate the position of the fixation target 602 in images 1 to 10 of the series of patient stimulus images 600. The offset between contiguous pairs of numerals and the frame rate at which the patient stimulus images are presented will cause the patients eye to achieve an angular velocity when tracking the fixation target 602. The angular velocity may be selected to simulate typical saccadic movement of the eye.

The saccadic movement of the eye 100 causes movement of the shadow 116. Upon fixation of the of the gaze of the eye 100, the shadow 116 and 202 slows down typically in one to two second. The settling time depends on the viscosity of the vitreous 110. The vitreous of the eye decreases with age. The settled position of the floater shadow can be called as home position of the shadow. The home position of the floater 114 and the floater shadow 116 and 202 is unchanged typically for several months. The movement of the shadow may cause one or more floater shadow 116 and 202 to pass over the fovea of the eye. Floaters shadows 116 and 202 that are not particularly irritating or noticeable when immobile may become so when set in motion. Accordingly, the position and offset of the fixation target positions in the series of images 600 may be selected to induce a range of movements in terms of angular velocity and direction in order to enable an accurate assessment of effect of the floater shadows 116 and 202 present in the patient's eyes 100.

Referring now to FIG. 8, in some implementations, the movement of the fixation target 602 between adjacent images of the series of patient stimulus images 600 is selected to cause the patient's eyes 100 to imitate movement of the eye 100 while reading. In this manner, the impact of floaters 114 on a common activity, such as reading, may be assessed. For example, the location of the fixation target 602 in the series of patient stimulus images 600 may traverse a horizontal path 800 from left to right at an angular velocity 802 (e.g., between 5 and 15 degrees per second), thereby simulating the movement of the eye while reading a line of text. The path 800 may be followed by a diagonal path 804 moving down and from right to left at a velocity 806 that is greater than the velocity 802 to simulate movement of the eye to focus on the beginning of a next line of text. For example, the path 804 may be traversed at an angular velocity 806 of between 80 and 120 degrees per second. Two, three, or more sets of paths 800, 804 may be combined (e.g., the illustrated five sets) in order to simulate the range of motion of the patient's eye 100 while reading.

Other patterns of movement of the fixation target 602 may be used to simulate various languages. For example, the path 800 may be from right to left and the diagonal path 804 may be from left to right and down for Hebrew, Arabic, or other Semitic languages. In another example, the path 800 is from top to bottom and the diagonal path 804 is from bottom to top and to the right for Japanese and some forms of Mandarin.

Figure 9:
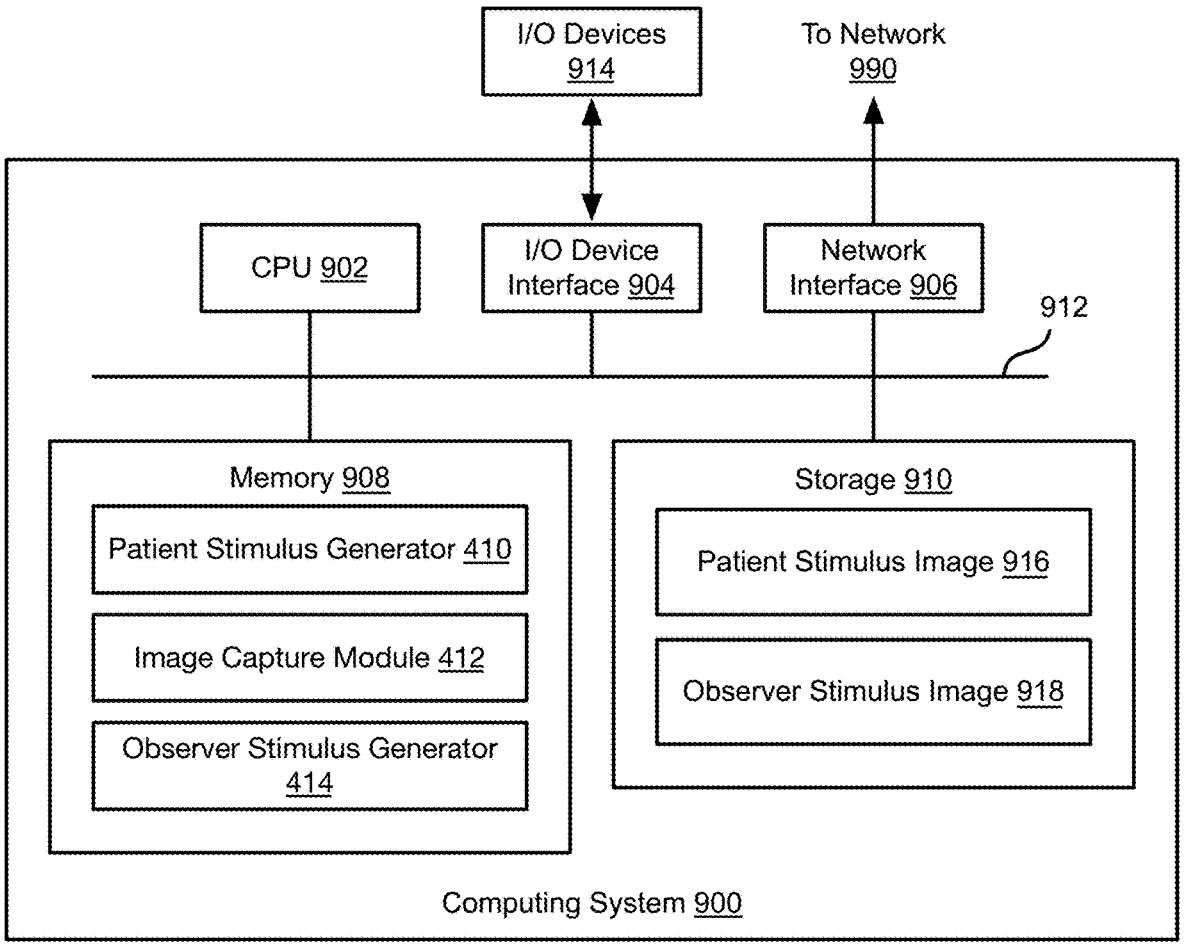
FIG. 9 illustrates an example computing device that implements, at least partly, one or more functionalities of performing psychophysical evaluation of vitreous floaters, in accordance with certain embodiments.

FIG. 9 illustrates an example computing system 900 that implements, at least partly, one or more functionalities described herein with respect to FIGS. 1 to 8. The computing system 900 may be integrated with an imaging device, such as the SLO 402, a display device 406, such as a VR display, or be a separate computing device receiving images of a patient's eye from the imaging device.

As shown, computing system 900 includes a central processing unit (CPU) 902, one or more I/O device interfaces 904, which may allow for the connection of various I/O devices 914 (e.g., keyboards, displays, mouse devices, pen input, etc.) to computing system 900, network interface 906 through which computing system 900 is connected to network 990, a memory 908, storage 910, and an interconnect 912.

In cases where computing system 900 is an imaging system, such as an SLO 402, computing system 900 may further include one or more optical components for obtaining ophthalmic imaging of a patient's eye as well as any other components known to one of ordinary skill in the art.

CPU 902 may retrieve and execute programming instructions stored in the memory 908. Similarly, CPU 902 may retrieve and store application data residing in the memory 908. The interconnect 912 transmits programming instructions and application data, among CPU 902, I/O device interface 904, network interface 906, memory 908, and storage 910. CPU 902 is included to be representative of a single CPU, multiple CPUs, a single CPU having multiple processing cores, and the like.

Memory 908 is representative of a volatile memory, such as a random access memory, and/or a nonvolatile memory, such as nonvolatile random access memory, phase change random access memory, or the like. As shown, memory 908 may store the patient stimulus generator 410, image capture module 412, and/or observer stimulus generator 414.

Storage 910 may be non-volatile memory, such as a disk drive, solid state drive, or a collection of storage devices distributed across multiple storage systems. Storage 910 may optionally store the patient stimulus image 916 and may also store the observer stimulus image 918 for subsequent display.

Additional Considerations

The preceding description is provided to enable any person skilled in the art to practice the various embodiments described herein. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s)

and/or module(s), including, but not limited to a circuit, an application specific integrated circuit (ASIC), or processor. Generally, where there are operations illustrated in figures, those operations may have corresponding counterpart means-plus-function components with similar numbering.

The various illustrative logical blocks, modules and circuits described in connection with the present disclosure may be implemented or performed with a general purpose processor, a digital signal processor (DSP), an application specific integrated circuit (ASIC), a field programmable gate array (FPGA) or other programmable logic device (PLD), discrete gate or transistor logic, discrete hardware components, or any combination thereof designed to perform the functions described herein. A general-purpose processor may be a microprocessor, but in the alternative, the processor may be any commercially available processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

A processing system may be implemented with a bus architecture. The bus may include any number of interconnecting buses and bridges depending on the specific application of the processing system and the overall design constraints. The bus may link together various circuits including a processor, machine-readable media, and input/output devices, among others. A user interface (e.g., keypad, display, mouse, joystick, etc.) may also be connected to the bus. The bus may also link various other circuits such as timing sources, peripherals, voltage regulators, power management circuits, and the like, which are well known in the art, and therefore, will not be described any further. The processor may be implemented with one or more general-purpose and/or special-purpose processors. Examples include microprocessors, microcontrollers, DSP processors, and other circuitry that can execute software. Those skilled in the art will recognize how best to implement the described functionality for the processing system depending on the particular application and the overall design constraints imposed on the overall system.

If implemented in software, the functions may be stored or transmitted over as one or more instructions or code on a computer-readable medium. Software shall be construed broadly to mean instructions, data, or any combination thereof, whether referred to as software, firmware, middleware, microcode, hardware description language, or otherwise. Computer-readable media include both computer storage media and communication media, such as any medium that facilitates transfer of a computer program from one place to another. The processor may be responsible for managing the bus and general processing, including the execution of software modules stored on the computer-readable storage media. A computer-readable storage medium may be coupled to a processor such that the processor can read information from, and write information to, the storage medium. In the alternative, the storage medium may be integral to the processor. By way of example, the computer-readable media may include a transmission line, a carrier wave modulated by data, and/or a computer readable storage medium with instructions stored thereon separate from the wireless node, all of which may be accessed by the processor through the bus interface. Alternatively, or in addition, the computer-readable media, or any portion thereof, may be integrated into the processor, such as the case may be with cache and/or general register files. Examples of machine-readable storage media may include, by way of example, RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The machine-readable media may be embodied in a computer-program product.

A software module may comprise a single instruction, or many instructions, and may be distributed over several different code segments, among different programs, and across multiple storage media. The computer-readable media may comprise a number of software modules. The software modules include instructions that, when executed by an apparatus such as a processor, cause the processing system to perform various functions. The software modules may include a transmission module and a receiving module. Each software module may reside in a single storage device or be distributed across multiple storage devices. By way of example, a software module may be loaded into RAM from a hard drive when a triggering event occurs. During execution of the software module, the processor may load some of the instructions into cache to increase access speed. One or more cache lines may then be loaded into a general register file for execution by the processor. When referring to the functionality of a software module, it will be understood that such functionality is implemented by the processor when executing instructions from that software module.

The following claims are not intended to be limited to the embodiments shown herein but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A method for characterizing floaters, comprising:
   receiving, by a computing device, one or more images of at least one of a patient's retinas, the one or more images captured while the at least one of the patient's retinas is stimulated with one or more patient stimulus images;
   identifying, by the computing device, one or more shaded regions in the one or more images to obtain one or more shadow images; and
   outputting, by the computing device, one or more observer stimulus images to a display device, the one or more observer stimulus images derived from the one or more shadow images and identical to a perception of the at least one of the patient's retinas of the one or more patient stimulus images.

2. The method of claim 1, wherein receiving the one or more images comprises receiving the one or more images from a scanning laser ophthalmoscope.

3. The method of claim 1, wherein the one or more patient stimulus images each include a fixation target.

4. The method of claim 3, wherein the one or more patient stimulus images include a series of patient stimulus images, wherein the fixation targets of the series of patient stimulus images are at a plurality of different locations.

5. The method of claim 4, wherein the plurality of different locations simulate eye movement while reading.

6. The method of claim 1, further comprising deriving the one or more observer stimulus images from the one or more shadow images by combining the one or more shadow images with the one or more patient stimulus images.

7. The method of claim 1, further comprising deriving the one or more observer stimulus images from the one or more shadow images by adjusting one or both of size and brightness of the one or more shadow images based on properties of the display device.

8. The method of claim 1, wherein the display device is a virtual reality display device.

9. The method of claim 8, wherein the one or more images comprise one or more left images of a left retina of the patient and one or more right images of a right retina of the patient; and
   wherein outputting the one or more observer stimulus images derived from the one or more shadow images to the display device comprises:
      outputting one or more left observer stimulus images of the one or more observer stimulus images on a left side of the virtual reality display device, the one or more left observer stimulus images derived from the one or more left images; and
      outputting one or more right observer stimulus images of the one or more observer stimulus images on a right side of the virtual reality display device, the one or more right observer stimulus images derived from the one or more right images.

10. A system for characterizing floaters comprising:
   a retinal imaging device;
   a display device; and
   a computing device configured to:
      receive one or more images of at least one of a patient's retinas from the retinal imaging device, the one or more images captured while the at least one of the patient's retinas is stimulated with one or more patient stimulus images;
      identify one or more shaded regions in the one or more images to obtain one or more shadow images; and
      output one or more observer stimulus images to the display device, the one or more observer stimulus images derived from the one or more shadow images and identical to a perception of the at least one of the patient's retinas of the one or more patient stimulus images.

11. The system of claim 10, wherein the retinal imaging device is a laser scanning ophthalmoscope.

12. The system of claim 10, wherein the one or more patient stimulus images each include a fixation target.

13. The system of claim 12, wherein the one or more patient stimulus images include a series of patient stimulus images, wherein the fixation targets of the series of patient stimulus images are at a plurality of different locations.

14. The system of claim 13, wherein the plurality of different locations simulates eye movement while reading.

15. The system of claim 10, wherein the computing device is further configured to derive the one or more observer stimulus images from the one or more shadow images by combining the one or more shadow images with the one or more patient stimulus images.

16. The system of claim 10, wherein the computing device is further configured to derive the one or more observer stimulus images from the one or more shadow images by adjusting one or both of size and brightness of the one or more shadow images based on properties of the display device.

17. The system of claim 10, wherein the display device is a virtual reality display device.

18. The system of claim 17, wherein the one or more images of the at least one of the patient's retinas comprise one or more left images of a left retina of the patient and one or more right images of a right retina of the patient;

wherein the computing device is configured to output the one or more observer stimulus images derived from the one or more shadow images to the display device by:

outputting one or more left observer stimulus images of the one or more observer stimulus images on a left side of the virtual reality display device, the one or more left observer stimulus images derived from the one or more left images; and outputting one or more right observer stimulus images of the one or more observer stimulus images on a right side of the virtual reality display device, the one or more right observer stimulus images derived from the one or more right images.

\* \* \* \* \*